(12) United States Patent
Martel et al.

(10) Patent No.: US 8,906,403 B2
(45) Date of Patent: Dec. 9, 2014

(54) BIOMATERIALS CARRYING CYCLODEXTRINS HAVING IMPROVED ABSORPTION PROPERTIES AND USED FOR THE PROGRESSIVE AND DELAYED RELEASE OF THERAPEUTIC MOLECULES

(75) Inventors: Bernard Martel, Nieppe (FR); Nicolas Blanchemain, Lumbres (FR); François Boschin, Bondues (FR); Stephan Haulon, Lille (FR); Elisabeth Delcourt Debruyne, Lambersart (FR); Michel Morcellet, Villeneuve d'Ascq (FR); Hartmut Friederich Hildebrand, Lille (FR)

(73) Assignees: Universite des Sciences et Technologies de Lille SAIC, Villeneuve d'ascq (FR); Universite de Droit et Sante, Lille (FR)

( * ) Notice: Subject to any disclaimer, the term of this patent is extended or adjusted under 35 U.S.C. 154(b) by 1540 days.

(21) Appl. No.: 11/719,386

(22) PCT Filed: Nov. 15, 2005

(86) PCT No.: PCT/FR2005/002829
§ 371 (c)(1),
(2), (4) Date: Aug. 27, 2007

(87) PCT Pub. No.: WO2006/051227
PCT Pub. Date: May 18, 2006

(65) Prior Publication Data
US 2008/0254094 A1    Oct. 16, 2008

(30) Foreign Application Priority Data

Nov. 15, 2004 (FR) ..................... 04 12086

(51) Int. Cl.
| | | |
|---|---|---|
| *A61L 27/54* | (2006.01) | |
| *A61K 47/34* | (2006.01) | |
| *A61K 47/32* | (2006.01) | |
| *A61K 47/36* | (2006.01) | |
| *A61K 47/38* | (2006.01) | |
| *A61L 27/56* | (2006.01) | |
| *A61L 31/16* | (2006.01) | |
| *A61L 29/16* | (2006.01) | |
| *A61L 31/10* | (2006.01) | |
| *A61L 27/34* | (2006.01) | |
| *A61L 31/14* | (2006.01) | |
| *A61L 29/14* | (2006.01) | |
| *A61L 29/08* | (2006.01) | |
| *A61K 47/48* | (2006.01) | |
| *B82Y 5/00* | (2011.01) | |

(52) U.S. Cl.
CPC .............. *A61L 29/146* (2013.01); *A61L 27/54* (2013.01); *A61L 27/56* (2013.01); *A61L 31/16* (2013.01); *A61L 29/16* (2013.01); *A61L 31/10* (2013.01); *A61L 27/34* (2013.01); *A61L 31/146* (2013.01); *A61L 2300/802* (2013.01); *A61L 29/085* (2013.01); *A61K 47/48969* (2013.01); *B82Y 5/00* (2013.01)

USPC .................... 424/424; 514/772.4; 514/772.3; 514/781; 514/777

(58) Field of Classification Search
None
See application file for complete search history.

(56) References Cited

U.S. PATENT DOCUMENTS

| 5,183,809 | A   |   | 2/1993  | Weisz et al. |
|-----------|-----|---|---------|--------------|
| 5,324,775 | A   | * | 6/1994  | Rhee et al. ................. 525/54.2 |
| 5,658,894 | A   | * | 8/1997  | Weisz ............................. 514/58 |
| 6,660,804 | B1  | * | 12/2003 | Weltrowski et al. ....... 525/54.23 |
| 6,689,378 | B1  |   | 2/2004  | Sun et al. |
| 6,712,846 | B1  | * | 3/2004  | Kraus et al. .................. 623/1.46 |
| 7,048,769 | B1  | * | 5/2006  | Weltrowski et al. ......... 8/115.51 |

FOREIGN PATENT DOCUMENTS

| DE | 19849464 A1 |   | 4/2000 |
|----|-------------|---|--------|
| EP | 1165621 B   |   | 10/2002 |
| EP | 1157156 B   |   | 4/2004 |
| FR | WO00/47811  | * | 8/2000 |
| WO | 01/85218 A  |   | 11/2001 |

OTHER PUBLICATIONS

Burgos et al. In Biomaterials 23 (2002) 2519-2526.*
Liu et al. in Journal of Material Science: Materials in Medicine 7 (1996) 551-557.*
Yue et al. in Biomaterials 25 (2004) 3743-3750.*
Natural Health Doc (http://healthy-information.natural healthdoc. net/STANDARD-PROCESS-INFORMATION-SHEET/Calcifood-Powder-Information.htm).*
Paste definition in www.thefreedictionary.com/paste (retrieved from the internet Feb. 17, 2014).*

* cited by examiner

*Primary Examiner* — Dennis Heyer
(74) *Attorney, Agent, or Firm* — Westerman, Hattori, Daniels & Adrian, LLP (57) ABSTRACT

A method for preparing a biomaterial containing at least one bioactive molecule from a base biomaterial, comprising the following successive operations carried out on the base biomaterial:
  a) application of a solid mixture of:
    cyclodextrin(s) and/or cyclodextrin derivative(s) and/or cyclodextrin inclusion complex(es) and/or cyclodextrin derivative inclusion complex(es),
    at least one poly(carboxylic) acid,
    and optionally a catalyst;
  b) heating at a temperature between 100° C. and 200° C. for a period of 1 to 60 minutes;
  c) washing with water;
  d) drying,
  wherein at least one bioactive agent is incorporated in the biomaterial by impregnation of the biomaterial after the drying step in a concentrated solution of the bioactive agent.

21 Claims, 3 Drawing Sheets

BIOMATERIALS CARRYING CYCLODEXTRINS HAVING IMPROVED ABSORPTION PROPERTIES AND USED FOR THE PROGRESSIVE AND DELAYED RELEASE OF THERAPEUTIC MOLECULES

The present invention relates to biomaterials carrying cyclodextrin with improved properties of absorption and of gradual and delayed release of therapeutic molecules, the method of preparation thereof as well as the use thereof as a prosthesis or an implant in particular.

The implantation of biomaterials in animals or humans can cause infection due to the introduction of pathogens during the surgical procedure. This phenomenon occurs in approximately 1% of vascular surgery cases and such complications can lead to the patient's death in approximately 50% of cases.

It is possible to combat this problem by a curative treatment using a biocide (antibiotic or antiseptic) or to fight the problem prophylactically by immersing the biomaterial in an antibiotic or antiseptic solution just prior to implantation. The active ingredient is then released in situ, directly in the susceptible area. However, this solution is imperfect in cases in which the nature of the material comprising the biomaterial is as follows:

the amount of active ingredient actually adsorbed by said material is very small, the active ingredient is released immediately within the organism (several minutes to several hours), and the concentration of the active ingredient rapidly decreases below the minimal inhibitory concentration (MIC).

The consequence is that the effectiveness of such systems is too limited over time with respect to the period of time during which possible infection is a risk (several weeks).

Various types of biomaterials allowing the controlled release (over time and/or in quantity) of active ingredients have been proposed.

In certain cases, the biomaterials are comprised of porous polymer matrices inside of which the active ingredient is contained. The active ingredient is released by diffusion from the pores of the matrix.

To this end, the document WO 02/41928 disclosed the use of a biomaterial containing a porous polymer comprised of an absorbent or amphiphilic polymer network (support network) whose pores contain a polymer gel containing one or more active ingredients (filling network). Preferably, the support network is a porous microsphere formed by acrylic copolymers modified by diethylaminoethyl groups. Example 3 of this document illustrates the comparative study of the release kinetics of indometacin and of various microspheres in conformity with the invention loaded with indometacin. The results presented in table II of this document show that although there is a gradual release of the quantity of active ingredient, the delay compared to the control microspheres (containing the active ingredient in the pores of the support network) is not significant.

In other cases, the biomaterials are comprised of biodegradable polymers which release the active ingredient(s) contained within the polymer matrix as the matrix degrades and is reabsorbed by the body. The release rate of the active ingredient depends on the degradation rate of the matrix.

Thus, the document U.S. Pat. No. 6,525,145 disclosed a biodegradable copolymer formed of polylactide and a polysaccharide such as dextran; prior to their copolymerization, at least one active ingredient is bound covalently to dextran. In an alternative embodiment, a second active ingredient can be incorporated noncovalently in the copolymer; this second active ingredient can be released by two different mechanisms:

by diffusion, before the copolymer degrades;

by release from the polymer matrix as the copolymer degrades.

According to the authors, release of the active ingredient(s) from said biomaterial can be modulated according to several criteria, namely:

the nature (hydrophilic or not) of the active ingredient covalently bound to the dextran;

the hydrolysis of the dextran molecule, which is a function of:

the nature of its glycosidic bonds (higher rate of hydrolysis for 1,6 bonds compared to 1,4 bonds);

the quantity of dextran incorporated in the copolymer.

However, since no study of the release kinetics of the active ingredient is included in the aforesaid document, it is difficult to evaluate the effectiveness of this controlled release system.

The present invention proposes to overcome the disadvantages presented by the various types of known biomaterials suitable for the gradual release of an active ingredient.

The invention relates to biomaterials carrying cyclodextrin that have an improved salting-out capacity in terms of the total amount of bioactive agent released, in terms of gradual release and in terms of the total duration of release of the bioactive agent. This invention calls upon the principle of grafting the biomaterial with cyclodextrin in such a way that the two adhere nearly permanently via covalent bonds or by physical interactions.

For this purpose, and according to a first aspect, the invention relates to a method of preparation of a biomaterial containing at least one bioactive molecule, from a base biomaterial, characterized by the following successive operations carried out on the aforesaid base biomaterial:

a) application of a solid mixture of:

cyclodextrin(s) and/or cyclodextrin derivative(s) and/or cyclodextrin inclusion complex(es) and/or cyclodextrin derivative inclusion complex(es), at least one poly(carboxylic) acid, and optionally a catalyst;

b) heating at a temperature between 100° C. and 220° C. for a period of 1 to 60 minutes;

c) washing with water;

d) drying, and wherein at least one bioactive agent is incorporated in the biomaterial by impregnation of the biomaterial after the drying step in a concentrated solution of bioactive agent.

According to a second aspect, the invention relates to a biomaterial prepared from a base biomaterial having a chemical structure which contains a hydroxyl function and/or an amine function, the aforesaid base structure being bound covalently to at least one molecule of cyclodextrin or to a polymer comprised of cyclodextrin whose structure contains the repetition of the motif of general formula:

$$[SB]-X{+}CO-[[Ac]-CO-O-[CD]-O{+}_n-$$
$$|$$
$$(COOH)_{x-y}$$

SB representing the structure of the base biomaterial comprised of a polymer material of natural or artificial origin and/or of a bioceramic material, X being either an oxygen atom belonging to an ester group or an NH group, with $x \geq 3$, $2 \leq y \leq (x-1)$ and $(x-y) \geq 1$, x being the number of carboxylic acid functions carried by the poly(carboxylic) acid before reaction, y representing the number of carboxylic acid functions of the poly(carboxylic) acid formed into esters or amides during the reaction, (x-y) being the number of carboxylic acid functions of the poly(carboxylic) acid not formed into esters or amides after reaction, $$—(COOH)_{x-y}$$
$$|$$
$$[Ac]$$

representing the molecular chain of a poly(carboxylic) acid of formula:

$$(COOH)_x$$
$$|$$
$$[Ac]$$

of which at least two carboxyl functions (—COOH) have undergone esterification or, respectively, esterification and amide formation and which carries at least one carboxyl function not having undergone an esterification or amide formation reaction;

[CD] representing the molecular structure of the cyclodextrins chosen preferentially among: α-cyclodextrin, β-cyclodextrin, γ-cyclodextrin and mixtures thereof; derivatives thereof which are preferentially selected among amino, methyl, hydroxypropyl, sulfobutyl, carboxymethyl or carboxyl derivatives and mixtures thereof; inclusion complexes of the aforesaid cyclodextrins or of the aforesaid cyclodextrin derivatives with bioactive molecules, wherein, the aforesaid biomaterial containing at least one bioactive agent forming a complex with the molecules of cyclodextrin and/or of cyclodextrin derivatives, the aforesaid bioactive agent is a therapeutic molecule.

According to a third aspect, the invention relates to a biomaterial prepared from a base biomaterial whose porous structure is occupied by, or the surface structure is coated or covered by a cross-linked polymer of cyclodextrin(s) and/or cyclodextrin derivative(s) and/or cyclodextrin inclusion complexes or cyclodextrin derivative inclusion complexes and whose structure contains the repetition of the motif of general formula:

$$—[[CD]-O-CO-[Ac]-CO-O-]_n-$$
$$|$$
$$(COOH)_{x-y}$$

with $x \geq 3$, $2 \leq y \leq (x-1)$ and $(x-y) \geq 1$, x being the number of carboxyl functions carried by the poly(carboxylic) acid before reaction, y representing the number of carboxyl functions of the poly(carboxylic) acid esterified during the reaction, (x-y) being the number of carboxyl functions of the poly(carboxylic) acid not esterified after reaction, $$—(COOH)_{x-y}$$
$$|$$
$$[Ac]$$

representing the molecular chain of a poly(carboxylic) acid of formula:

$$(COOH)_x$$
$$|$$
$$[Ac]$$

of which at least two carboxyl functions (—COOH) have undergone esterification and which carries at least one carboxyl function not having undergone an esterification reaction;

[CD] representing the molecular structure of the cyclodextrins chosen preferentially among: α-cyclodextrin, β-cyclodextrin, γ-cyclodextrin and mixtures thereof; derivatives thereof which are preferentially selected among amino, methyl, hydroxypropyl, sulfobutyl, carboxymethyl or carboxyl derivatives and mixtures thereof; inclusion complexes of the aforesaid cyclodextrins or of the aforesaid cyclodextrin derivatives with bioactive molecules, wherein, the aforesaid biomaterial containing at least one bioactive agent forming a complex with the molecules of cyclodextrin and/or of cyclodextrin derivatives, the aforesaid bioactive agent is a therapeutic molecule.

According to a fourth aspect, the invention relates to the use of a biomaterial such as defined previously as an implant, prosthesis or device for the controlled release of at least one therapeutic molecule.

The invention now will be disclosed in detail.

The present invention relates to novel types of biomaterials carrying cyclodextrin in a complex with at least one bioactive agent which have improved salting-out capacity in terms of the total amount of bioactive agent released, in terms of gradual release and in terms of the total duration of release of the bioactive agent.

The goal of this new functionality is to appreciably reduce the risks of post-operative infections related to the colonization of the wound or the graft by pathogenic bacteria during a critical period which can range from 6 to 8 weeks.

As a consequence, these conditions justify the design of a biomaterial capable of absorbing a sufficient quantity of bioactive agent which can then be released gradually during this critical period.

The invention calls upon the principle of grafting the biomaterial with cyclodextrin (CD) in such a way that the two adhere nearly permanently via covalent bonds or by physical interactions. In this case, cyclodextrin forms an integral part of the base biomaterial.

In one embodiment, at least one bioactive agent is subsequently incorporated with the grafted base biomaterial by impregnation in a concentrated solution of bioactive agent, an operation during which said bioactive agent comes to be included within the cavities of the cyclodextrin present on the biomaterial.

In another embodiment, the cyclodextrin-bioactive agent inclusion complex is formed first and then subsequently grafted onto the base biomaterial.

"Biomaterial" means any non-living material, of natural or artificial origin, tolerated by humans or animals, in contact with the organism for more than several weeks, used in the production of a medical device intended to be placed in contact with biological tissues (skin, teeth, bones, blood, etc.) for the purpose of replacing or treating a tissue, organ or function.

The base biomaterial is a biomaterial which does not contain bioactive molecules.

Binding of the cyclodextrin molecules(s) on the base biomaterial is primarily carried out via two mechanisms, each of which depends on the chemical nature of said biomaterial.

In the case of the treatment of base biomaterials having a chemical structure containing a hydroxyl and/or amine function, the method of the invention allows the initial formation of an anhydride of the poly(carboxylic) acid which reacts with the biomaterial by forming an amide or ester covalent bond between the treated biomaterial and the poly(carboxylic) acid. Then, in the simplest case, a second anhydride of the poly(carboxylic) acid already bound to the biomaterial is formed, said anhydride then reacting with a molecule of cyclodextrin or of cyclodextrin derivative by creating an ester bond with the molecule of cyclodextrin or of cyclodextrin derivative.

Certain synthetic or mineral polymer biomaterials, however, do not possess functional groups capable of reacting according to the mechanism proposed above. In this case, the binding of cyclodextrin(s) and/or cyclodextrin derivatives(s) is carried out by the formation of a cross-linked polymer obtained by exclusive reaction between the cyclodextrin and/or cyclodextrin derivative molecule(s) and at least one poly (carboxylic) acid. The cross-linked polymer thus formed forms a film or a deposition on the surface of the base biomaterial, or is confined within its porous structure, and remains bound there permanently, according to the structure of the treated biomaterial.

When the polymer:

is formed from a molecule of cyclodextrin bound to the structure of the base biomaterial by a covalent bond, it has at least one covalent bond with the base biomaterial.

When the copolymer:

is formed from molecules of poly(carboxylic) acid and cyclodextrin and/or cyclodextrin derivative(s) not bound to the base structure of the biomaterial, it can nevertheless, if it is cross-linked, i.e., if it forms a three-dimensional network intermingling with or coating the structure of the base biomaterial, be physically and permanently bound to said biomaterial.

The base mechanism utilizing a molecule of poly(carboxylic) acid and a molecule of cyclodextrin or of cyclodextrin derivative was disclosed by the applicant in previous patents EP 1,165,621 and EP 1,157,156.

In the case of a polymer base biomaterial containing an amine or hydroxyl function such as, for example, chitosan, keratin, cellulose or derivatives thereof, the two binding mechanisms, namely formation of a film via covalent bonds and coating of the biomaterial with a cross-linked polymer, may coexist.

According to a preferred embodiment, the application of the solid mixture is obtained by impregnation of the material with an aqueous solution of:
- cyclodextrin(s) and/or cyclodextrin derivative(s) or cyclodextrin inclusion complexes or cyclodextrin-bioactive agent inclusion complexes,
- at least one poly(carboxylic) acid,
- and optionally a catalyst,
then drying of the impregnated base biomaterial.

Said impregnation and said drying make it possible to uniformly deposit the reagents on the surface of the base biomaterial or within its pores, a characteristic which later facilitates both the cyclodextrin binding reaction and the obtaining of a uniform deposition or coating of polymer on the surface or in the pores of the base biomaterial.

According to a preferred embodiment, the base biomaterial is pre-dried at a temperature between 40° C. and 90° C., preferably, before the primary heating operation which is carried out at a temperature between 100° C. and 220° C. for a period of time ranging from 1 to 60 minutes.

Primary heating is intended to permanently bind the cyclodextrin molecules(s) to the base biomaterial by a reaction between the poly(carboxylic) acid and the base biomaterial, according to at least one of the following mechanisms:
- chemical grafting by covalent bonds between the structure of the base biomaterial and the molecule of cyclodextrin or cyclodextrin derivative optionally in a complex with at least one bioactive molecule, or with a polymer of cyclodextrin(s) and poly(carboxylic) acid(s);
- reaction between the poly(carboxylic) acid and the cyclodextrin and/or the cyclodextrin derivative(s) or inclusion complexes thereof with bioactive molecules to form a cross-linked copolymer (physical grafting by coating).

Preferably, the polycarboxylic acid is selected among acyclic poly(carboxylic) acids, saturated and unsaturated cyclic poly(carboxylic) acids, saturated and unsaturated aromatic poly(carboxylic) acids, hydroxypoly(carboxylic)acids, preferably citric acid, polyacrylic acid, poly(methacrylic) acid, 1,2,3,4-butanetetracarboxylic acid, maleic acid, citraconic acid, itaconic acid, 1,2,3-propanetricarboxylic acid, trans-aconitic acid, all-cis-1,2,3,4-cydopentanetetracarboxylic acid, mellitic acid, oxydisuccinic acid and thiodisuccinic acid.

Anhydride derivatives of the above-named acids may also be used.

Preferably, the mixture contains a catalyst chosen among dihydrogen phosphates, hydrogen phosphates, phosphates, hypophosphites, alkaline metal phosphites, polyphosphoric acid alkaline metal salts, carbonates, bicarbonates, acetates, borates, alkaline metal hydroxides, aliphatic and ammonia amines, preferably among sodium hydrogen phosphate, sodium dihydrogen phosphate and sodium hypophosphite.

Preferably, the cyclodextrin is selected among: α-cyclodextrin, β-cyclodextrin, γ-cyclodextrin and mixtures thereof; cyclodextrin derivatives selected among the amino, methyl, hydroxypropyl, sulfobutyl, carboxymethyl or carboxyl derivatives of α-cyclodextrin, β-cyclodextrin and γ-cyclodextrin, and mixtures thereof; and inclusion complexes of the aforesaid cyclodextrins or of the aforesaid cyclodextrin derivatives with bioactive molecules.

According to a second aspect, the invention relates to a biomaterial prepared, preferably, by the method according to the invention from a base biomaterial having a chemical structure which contains a hydroxyl function and/or an amine function, the aforesaid base structure being bound covalently to at least one molecule of cyclodextrin or to a polymer comprised of cyclodextrin whose structure contains the repetition of the motif of general formula:

SB representing the structure of the base biomaterial comprised of a polymer material of natural or artificial origin and/or of a bioceramic material or a polyol, X being either an oxygen atom or an NH group, with $x \geq 3$, $2 \leq y \leq (x-1)$ and $(x-y) \geq 1$,
x being the number of carboxyl functions carried by the poly(carboxylic) acid before reaction,
y representing the number of carboxyl functions of the poly(carboxylic) acid formed into esters or amides during the reaction,
(x−y) being the number of carboxyl functions of the poly (carboxylic) acid not formed into esters or amides after reaction, representing the molecular chain of a poly(carboxylic) acid of formula:

of which at least two carboxyl functions (—COOH) have undergone esterification or, respectively, esterification and amide formation and which carries at least one carboxyl function not having undergone an esterification or amide formation reaction;
  [CD] representing the molecular structure of the cyclodextrins chosen preferentially among: α-cyclodextrin, β-cyclodextrin, γ-cyclodextrin and mixtures thereof; derivatives thereof which are preferentially selected among amino, methyl, hydroxypropyl, sulfobutyl, carboxymethyl or carboxyl derivatives and mixtures thereof; inclusion complexes of the aforesaid cyclodextrins or of the aforesaid cyclodextrin derivatives with bioactive molecules,
wherein, the aforesaid biomaterial containing at least one bioactive agent forming a complex with the molecules of cyclodextrin and/or of cyclodextrin derivatives, the aforesaid bioactive agent is a therapeutic molecule.

"Therapeutic molecule" means any molecule intended for prophylaxis and/or treatment of human or animal diseases.

According to a third aspect, the invention relates to a biomaterial prepared, preferably, by the method according to the invention from a base biomaterial whose porous structure is occupied by, or the surface structure is coated or covered by a cross-linked polymer of cyclodextrin(s) and/or cyclodextrin derivative(s) and/or cyclodextrin inclusion complexes or cyclodextrin derivative inclusion complexes and whose structure contains the repetition of the motif of general formula:

with $x \geq 3$, $2 \leq y \leq (x-1)$ and $(x-y) \geq 1$,
x being the number of carboxyl functions carried by the poly(carboxylic) acid before reaction,
y representing the number of carboxyl functions of the poly(carboxylic) acid esterified during the reaction,
(x−y) being the number of carboxyl functions of the poly (carboxylic) acid not esterified after reaction, representing the molecular chain of a poly(carboxylic) acid of formula:

of which at least two carboxyl functions (—COOH) have undergone esterification and which carries at least one carboxyl function not having undergone an esterification reaction;
  [CD] representing the molecular structure of the cyclodextrins chosen preferentially among: α-cyclodextrin, β-cyclodextrin, γ-cyclodextrin and mixtures thereof; derivatives thereof which are preferentially selected among amino, methyl, hydroxypropyl, sulfobutyl, carboxymethyl or carboxyl derivatives and mixtures thereof; inclusion complexes of the aforesaid cyclodextrins or of the aforesaid cyclodextrin derivatives with bioactive molecules,
wherein, the aforesaid biomaterial containing at least one bioactive agent forming a complex with the molecules of cyclodextrin and/or of cyclodextrin derivatives, the aforesaid bioactive agent is a therapeutic molecule.

Thus, the present invention relates to biomaterials prepared from base biomaterials on which cyclodextrin and/or cyclodextrin derivative molecule(s) are bound by covalent bonds alone, biomaterials prepared from base biomaterials on which cyclodextrin and/or cyclodextrin derivative molecule(s) are bound both by covalent bonds and by occupation of the porous structure, or by coating or covering of the surface structure of the base biomaterial by a cross-linked polymer of cyclodextrin(s), and biomaterials prepared from base biomaterials on which cyclodextrin is bound by occupation of the porous structure alone, or by coating or covering of the surface structure of the base biomaterial by a cross-linked polymer of cyclodextrin(s) alone.

The biomaterial can be functionalized with a bioactive agent according to the invention by various mechanisms.

In an alternative embodiment, the base biomaterial is grafted with the cyclodextrin and/or cyclodextrin derivative molecule(s) according to one of the embodiments disclosed above and is then impregnated in a concentrated solution of the bioactive agent. The purpose of this operation is to place the grafted cyclodextrin in the presence of the bioactive agent, an operation which results in the formation of a "host-guest" formation complex. Thus, a biomaterial is obtained loaded with the active ingredient which will then be released in a slowed-down manner once said biomaterial is implanted in the organism.

In another embodiment, the base biomaterial is grafted with a cyclodextrin-bioactive agent inclusion complex or a cyclodextrin derivative-bioactive agent inclusion complex previously prepared according to techniques of the art. Thus, in the production process, it suffices to replace the cyclodextrin by the cyclodextrin-bioactive agent complex.

The present invention makes it possible to draw upon some characteristics of the cyclodextrin complex by grafting said complex on the base biomaterial by establishing a covalent chemical bond or by depositing a cyclodextrin polymer that adheres to the biomaterial by physical interactions.

The chemical or physical grafting of cyclodextrin on the base biomaterial has the advantage that the former remains present on the latter and is not detached from it by immediate dissolution in the physiological medium in which the biomaterial is implanted.

The biomaterials according to the invention have the capacity to absorb in an increased manner and to release in a prolonged manner bioactive substances such as anticoagulants, antithrombotics, antimitotics, antiproliferation agents, antiadhesion agents, antimigration agents, cell adhesion promoters, growth factors, antiparasitic molecules, anti-inflammatories, anti-angiogenics, angiogenesis inhibiters, vitamins, hormones, proteins, antifungals, antimicrobial molecules, antiseptics or antibiotics.

Increased absorption capacity by the bioactive molecules is due to the fact that grafted cyclodextrins are complex-formation sites which actively form these bioactive molecules into complexes, in contrast to non-grafted surfaces which exhibit only nonspecific interactions with substrates (ionic hydrogen bonds and Van der Waals bonds).

Delayed release is due to action by the cyclodextrin which has the property of forming host-guest inclusion complexes with the above-mentioned molecules and releasing the guest in a slowed-down, gradual manner.

In addition, it is known that a given therapeutic agent exhibits different complex formation equilibrium constants depending on the nature of the cyclodextrins used ($\alpha$, $\beta$, $\gamma$, hydroxypropyl-$\alpha$, etc.). As a result, each type of cyclodextrin bound to the base biomaterial will release the therapeutic agent more or less rapidly according to its own kinetics. Consequently, it will be possible to modulate the release kinetics of a bioactive agent by using a mixture of several cyclodextrins during grafting on the base biomaterial and by adjusting the proportion of each cyclodextrin in said mixture.

In addition, because carboxyl functions (or carboxylate functions, according to the pH of the medium) are present on the biomaterials according to the invention, said functions can be used as ion exchangers. Thus, the $H^+$ ion of a carboxyl function (or the $Na^+$ of a carboxylate function) can be substituted by another cation, chosen for example from the group comprised of silver ions, quaternary ammonium ions and chlorhexidine hydrochloride, all known for their biocidal properties.

The impregnation of the biomaterial according to the invention with a solution of a cationic biocidal compound (performed after the drying step) makes it possible to confer biocidal properties to said biomaterial; the biomaterial binds the biocidal agent by an ion exchange mechanism. The biomaterial thus treated will exhibit additional properties that are distinct or indistinct from those already conferred by the therapeutic agent in a complex with cyclodextrins. Persons skilled in the art will be able to decide, according to the therapeutic agent to be released or to the biocidal agent to be bound, to use one of these functions alone or several simultaneously. The latter case corresponds, for example, to chlorhexidine hydrochloride, a compound which is both aromatic (thus suitable for inclusion in cyclodextrins) and cationic (thus suitable for binding to carboxyl groups). In this case, the same bioactive agent will be released in vivo according to two different mechanisms.

According to a fourth aspect, the invention relates to the use of a biomaterial as defined previously as an implant, prosthesis or device for the controlled release of at least one therapeutic molecule.

The present invention relates to the use of biomaterials carrying cyclodextrin in a complex with at least one bioactive agent as vascular prostheses and endoprostheses (coated stents); hernia supports; guided tissue regeneration membranes; guided bone regeneration membranes; intrasulcular release devices; dialysis, perfusion, transfusion or artificial nutrition tubes and catheters; transcutaneous implants; tissue engineering lattices and networks; micro- and macro-porous bone substitutes; and suture and bandage wire or threads for medical or veterinary use.

The structure of the base biomaterial according to the invention can consist of polymer material such as polyethylene terephthalate glycol (PETG), polylactic acid (PLA), polyglycolic acid (PGA) and copolymers thereof (PLGA), polyvinylidene fluoride (PVDF), polytetrafluoroethylene (PTFE), cellulose, oxidized cellulose, regenerated cellulose, polyethylene glycol (PEG), polyamide-6, polyamide-6,6, polypropylene, polyethylene, polysaccharides such as pectin, carrageenans, alginates and dextrans, keratin, chitosan, collagen, gelatin or a combination of said polymers.

In other embodiments, the structure of the base biomaterial according to the invention is comprised of mineral compounds such as bioceramics, including calcium phosphates, hydroxyapatites, alumina, zirconia, glass and ionomer glass.

In other embodiments, the structure of the base biomaterial according to the invention is comprised of composites that are combinations of the mineral compounds and polymer materials defined above.

The invention also relates to devices for the controlled release of at least one therapeutic molecule comprised of at least one biomaterial such as defined above.

The invention also relates to compositions containing at least one biomaterial such as defined above.

The present invention will be better understood upon consideration of the following examples, which are given in a non-limiting manner for the purpose of better illustrating the characteristics of the biomaterials according to the present invention.

EXAMPLE 1

Using a foulard, a sample of woven PET vascular prosthesis was impregnated with an aqueous solution containing $\beta$-CD (100 g/l), citric acid (80 g/l) and sodium hypophosphite (10 g/l). Pick-up was 70%. The sample was then dried for 7 minutes at 90° C., treated for 30 minutes at 140° C., washed with water using a soxhlet and dried. Weight increase due to grafting was 2.4%.

EXAMPLE 2

Using a foulard, a sample of woven PET vascular prosthesis was impregnated with an aqueous solution containing β-CD (100 g/l), citric acid (80 g/l) and sodium hypophosphite (10 g/l). Pick-up was 70%. The sample was then dried for 7 minutes at 90° C., treated for 30 minutes at 150° C., washed with water using a soxhlet and dried. Weight increase due to grafting was 7.4%.

EXAMPLE 3

Using a foulard, a sample of woven PET vascular prosthesis was impregnated with an aqueous solution containing β-CD (100 g/l), citric acid (80 g/l) and sodium hypophosphite (10 g/l). Pick-up was 70%. The sample was then dried for 7 minutes at 90° C., treated for 30 minutes at 160° C., washed with water using a soxhlet and dried. Weight increase due to grafting was 9.2%.

EXAMPLE 4

Using a foulard, a sample of woven PET vascular prosthesis was impregnated with an aqueous solution containing β-CD (100 g/l), citric acid (80 g/l) and sodium hypophosphite (10 g/l). Pick-up was 70%. The sample was then dried for 7 minutes at 90° C., treated for 30 minutes at 170° C., washed with water using a soxhlet and dried. Weight increase due to grafting was 9.9%.

EXAMPLE 5

Using a foulard, a sample of woven PET vascular prosthesis was impregnated with an aqueous solution containing β-CD (100 g/l), citric acid (80 g/l) and sodium hypophosphite (10 g/l). Pick-up was 70%. The sample was then dried for 7 minutes at 90° C., treated for 5 minutes at 170° C., washed with water using a soxhlet and dried. Weight increase due to grafting was 8.8%.

EXAMPLE 6

Using a foulard, a sample of woven PET vascular prosthesis was impregnated with an aqueous solution containing β-CD (100 g/l), 1,2,3,4-butanetetracarboxylic acid (80 g/l) and sodium hypophosphite (10 g/l). Pick-up was 70%. The sample was then dried for 7 minutes at 90° C., treated for 6 minutes at 175° C., washed with water using a soxhlet and dried. Weight increase due to grafting was 25%.

EXAMPLE 7

Using a foulard, a sample of woven PET vascular prosthesis was impregnated with an aqueous solution containing hydroxypropyl-β-cyclodextrin (100 g/l), citric acid (80 g/l) and sodium hypophosphite (10 g/l). Pick-up was 70%. The sample was then dried for 7 minutes at 90° C., treated for 10 minutes at 140° C., washed with water using a soxhlet and dried. Weight increase due to grafting was 5%.

EXAMPLE 8

Using a foulard, a sample of woven PET vascular prosthesis was impregnated with an aqueous solution containing hydroxypropyl-β-cyclodextrin (100 g/l), citric acid (80 g/l) and sodium hypophosphite (10 g/l). Pick-up was 70%. The sample was then dried for 7 minutes at 104° C., treated for 10 minutes at 150° C., washed with water using a soxhlet and dried. Weight increase due to grafting was 11.1%.

EXAMPLE 9

Using a foulard, a sample of woven PET vascular prosthesis was impregnated with an aqueous solution containing hydroxypropyl-γ-cyclodextrin (100 g/l), citric acid (80 g/l) and sodium hypophosphite (10 g/l). Pick-up was 70%. The sample was then dried for 7 minutes at 90° C., treated for 10 minutes at 160° C., washed with water using a soxhlet and dried. Weight increase due to grafting was 10%.

EXAMPLE 10

Using a foulard, a sample of woven PET vascular prosthesis was impregnated with an aqueous solution containing hydroxypropyl-γ-cyclodextrin (100 g/l), citric acid (80 g/l) and sodium hypophosphite (10 g/l). Pick-up was 70%. The sample was then dried for 7 minutes at 90° C., treated for 5 minutes at 150° C., washed with water using a soxhlet and dried. Weight increase due to grafting was 6.5%.

EXAMPLE 11

Using a foulard, a sample of woven PET vascular prosthesis was impregnated with an aqueous solution containing hydroxypropyl-γ-cyclodextrin (100 g/l), citric acid (80 g/l) and sodium hypophosphite (10 g/l). Pick-up was 70%. The sample was then dried for 7 minutes at 90° C., treated for 10 minutes at 150° C., washed with water using a soxhlet and dried. Weight increase due to grafting was 8.1%.

EXAMPLE 12

Using a foulard, a sample of woven PET vascular prosthesis was impregnated with an aqueous solution containing hydroxypropyl-γ-cyclodextrin (100 g/l), citric acid (80 g/l) and sodium hypophosphite (10 g/l). Pick-up was 70%. The sample was then dried for 7 minutes at 90° C., treated for 15 minutes at 150° C., washed with water using a soxhlet and dried. Weight increase due to grafting was 11%.

EXAMPLE 13

Using a foulard, a PVDF microporous membrane was impregnated with an aqueous solution containing β-CD (100 g/l), citric acid (100 g/l) and sodium hypophosphite (30 g/l). Pick-up was 60%. The sample was then dried for 3 minutes at 90° C., treated for 10 minutes at 140° C., washed with water using a soxhlet and dried. Weight increase due to grafting was 2.4%.

EXAMPLE 14

Using a foulard, a PVDF microporous membrane was impregnated with an aqueous solution containing β-CD (100 g/l), citric acid (100 g/l) and sodium hypophosphite (30 g/l). Pick-up was 86%. The sample was then dried for 3 minutes at 90° C., treated for 10 minutes at 150° C., washed with water using a soxhlet and dried. Weight increase due to grafting was 10.5%.

EXAMPLE 15

Using a foulard, a PVDF microporous membrane was impregnated with an aqueous solution containing β-CD (100 g/L), citric acid (100 g/l) and sodium hypophosphite (30 g/l). Pick-up was 78%. The sample was then dried for 3 minutes at 90° C., treated for 10 minutes at 170° C., washed with water using a soxhlet and dried. Weight increase due to grafting was 15.5%.

EXAMPLE 16

Using a foulard, a PVDF microporous membrane was impregnated with an aqueous solution containing hydroxypropyl-β-cyclodextrin (100 g/l), citric acid (100 g/l) and sodium hypophosphite (30 g/l). Pick-up was 85%. The sample was then dried for 3 minutes at 90° C., treated for 10 minutes at 170° C., washed with water using a soxhlet and dried. Weight increase due to grafting was 15.8%.

EXAMPLE 17

Using a foulard, a microporous regenerated cellulose membrane was impregnated with an aqueous solution containing β-CD (100 g/l), citric acid (100 g/l) and sodium hypophosphite (30 g/l). Pick-up was 163%. The sample was then dried for 3 minutes at 90° C., treated for 10 minutes at 170° C., washed with water using a soxhlet and dried. Weight increase due to grafting was 3.95%.

EXAMPLE 18

Using a foulard, a microporous regenerated cellulose membrane was impregnated with an aqueous solution containing β-CD (100 g/l), citric acid (100 g/l) and sodium hypophosphite (30 g/l). Pick-up was 187%. The sample was then dried for 3 minutes at 90° C., treated for 10 minutes at 150° C., washed with water using a soxhlet and dried. Weight increase due to grafting was 14.9%.

EXAMPLE 19

Using a foulard, a sample of polyamide-6 fabric was impregnated with an aqueous solution containing β-CD (100 g/l), citric acid (100 g/l) and sodium hypophosphite (30 g/l). Pick-up was 70%. The sample was then dried for 3 minutes at 104° C., treated for 3 minutes at 170° C., washed with water using a soxhlet and dried. Weight increase due to grafting was 5%.

EXAMPLE 20

Using a foulard, a sample of polyamide-6 fabric was impregnated with an aqueous solution containing β-CD (100 g/l), citric acid (100 g/l) and sodium hypophosphite (30 g/l). Pick-up was 70%. The sample was then dried for 3 minutes at 104° C., treated for 5 minutes at 170° C., washed with water using a soxhlet and dried. Weight increase due to grafting was 10%.

EXAMPLE 21

Using a foulard, a sample of polyamide-6 fabric was impregnated with an aqueous solution containing β-CD (100 g/l), citric acid (100 g/l) and sodium hypophosphite (30 g/l). Pick-up was 70%. The sample was then dried for 3 minutes at 104° C., treated for 12 minutes at 170° C., washed with water using a soxhlet and dried. Weight increase due to grafting was 12.5%.

EXAMPLE 22

This example illustrates the capacities for increased absorption and delayed release of a PVDF membrane functionalized by β-CD with respect to chlorhexidine, an antiseptic chosen as the active ingredient. In a first step, one untreated membrane and one membrane functionalized by β-CD were plunged into a chlorhexidine solution (0.04 g/l). In a second step, both membranes loaded with chlorhexidine were rinsed with water and then plunged into a physiological medium maintained at 37° with agitation. The evolution of the chlorhexidine concentration in the medium was then measured by UV-visible spectrophotometry at 255 nm.

Figure 1:
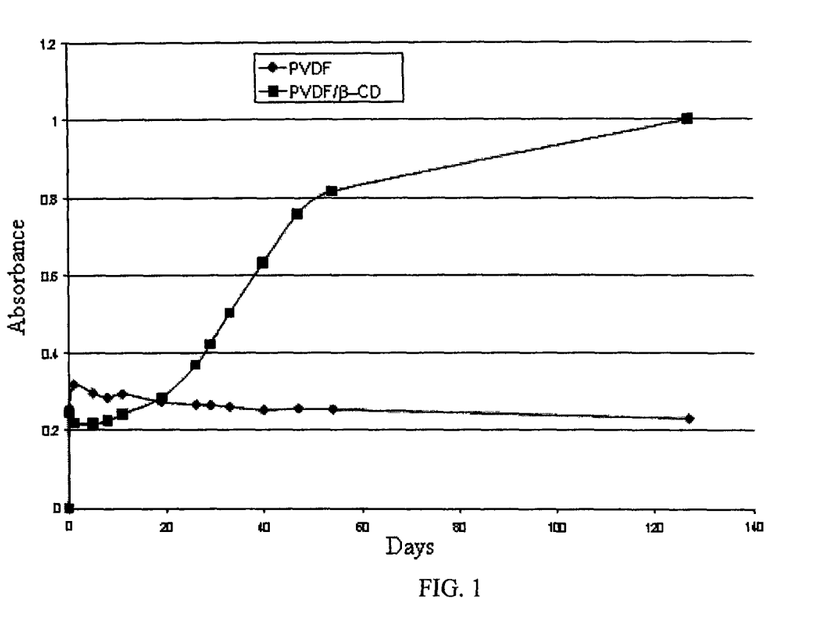
FIG. 1 shows the evolution of the quantity of chlorhexidine released over a period of 180 days by an untreated membrane and a membrane functionalized with β-cyclodextrin.

FIG. 1 represents the evolution of the quantity of chlorhexidine released in the medium by the two membranes over a period of 130 days.

EXAMPLE 23

This example illustrates the capacities for increased absorption and delayed release of a woven PET vascular prosthesis functionalized by β-CD with respect to vancomycin, an antibiotic chosen as the active ingredient. In a first step, one untreated membrane and one membrane functionalized by β-CD with a grafting rate of 10% were plunged into a vancomycin solution (5 g/l). In a second step, both membranes loaded with vancomycin were rinsed with water and then plunged into a physiological medium maintained at 370 with agitation. The evolution of the vancomycin concentration in the medium was then measured by UV-visible spectrophotometry at 280 nm.

Figure 2:
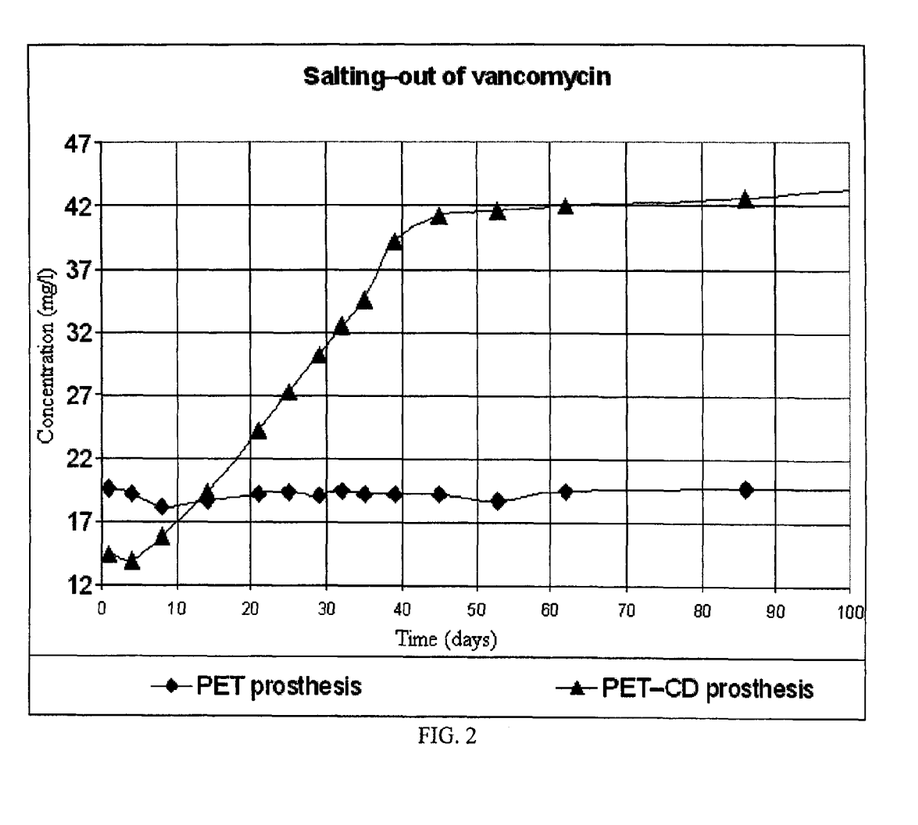
FIG. 2 shows the evolution of the concentration of vancomycin released over a period of 86 days by an untreated woven PET vascular prosthesis and a woven PET vascular prosthesis functionalized with β-cyclodextrin.

FIG. 2 represents the evolution of the vancomycin concentration (in mg/l) released in the medium by the two prostheses over a period of 86 days.

EXAMPLE 24

Figure 3:
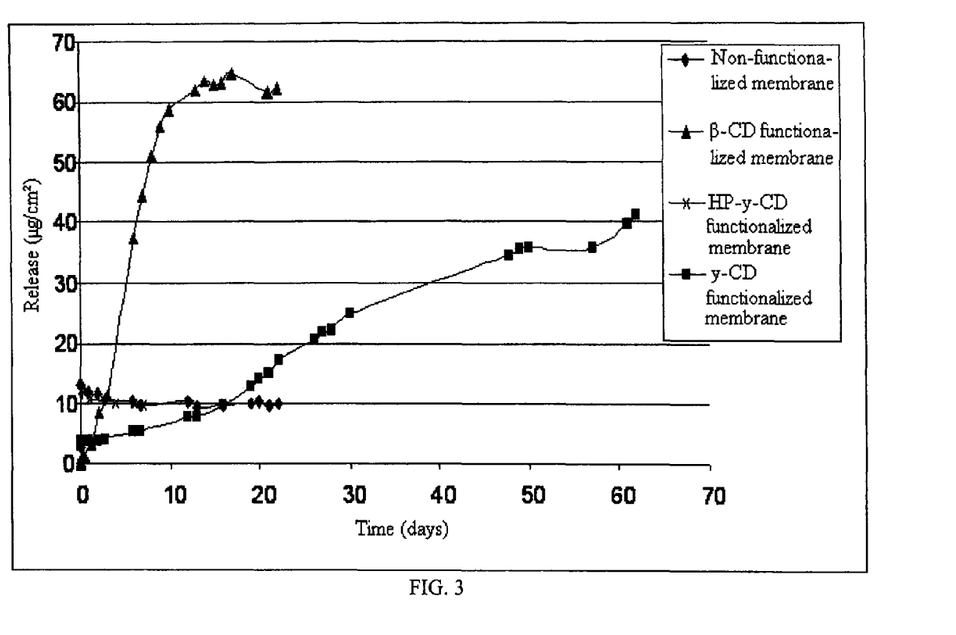
FIG. 3 shows the release of chlorhexidine by microporous PVDF membranes functionalized with β-cyclodextrin, hydroxylpropyl-γ-cyclodextrin, and γ-cyclodextrin, respectively.

This example illustrates the possibility of modulating the release kinetics of a bioactive agent by using a mixture of several cyclodextrins during grafting on the base biomaterial and by adjusting the proportion of each cyclodextrin in said mixture. FIG. 3 represents the study of chlorhexidine release by microporous PVDF membranes functionalized by three different cyclodextrins: β-cyclodextrin, hydroxypropyl-γ-cyclodextrin and γ-cyclodextrin. The results obtained show that chlorhexidine is released in the first ten days when the membrane is grafted with γ-cyclodextrin; this period is greater than 60 days for β-cyclodextrin. On the other hand, hydroxypropyl-γ-cyclodextrin is ineffective; it yields the same result as the untreated membrane, used as a control, which releases all of the chlorhexidine immediately.

The invention claimed is:

1. A device for controlled release of at least one bioactive agent, wherein said device is an implant or a prosthesis and comprises at least one biomaterial comprising a base biomaterial modified by forming a cross-linked polymer bound to the base biomaterial by polymerizing onto the base material (1) a polycarboxylic acid of general formula wherein x≥3 and [Ac] is an organic moiety bearing x COOH groups with (2) at least one cyclodextrin monomer represented by general formula wherein [CD] is a cyclodextrin moiety bearing z OH groups, wherein the cyclodextrin monomer is at least one member selected from the group consisting of α-cyclodextrin; β-cyclodextrin; γ-cyclodextrin; amino, methyl, hydroxypropyl, sulfobutyl, carboxymethyl or carboxyl derivatives of α-cyclodextrin; amino, methyl, hydroxypropyl, sulfobutyl, carboxymethyl or carboxyl derivatives of β-cyclodextrin; amino, methyl, hydroxypropyl, sulfobutyl, carboxymethyl or carboxyl derivatives of γ-cyclodextrin; inclusion complexes of α-cyclodextrin, β-cyclodextrin, γ-cyclodextrin or said derivatives with bioactive molecules, wherein the cross-linked polymer contains a repetition of the motif of general formula:

wherein 2≤y≤(x−1), (x−y)≥1, and t≥2, y represents the number of carboxyl functions of the poly (carboxylic) acid esterified during polymerization, (x−y) represents the number of carboxyl functions of the poly(carboxylic) acid not esterified after polymerization, z represents the number of OH groups carried by the CD unit before esterification with the polycarboxylic acid, t represents the number of OH groups of the CD unit that underwent esterification with the polycarboxylic acid, (z−t) represents the remaining OH groups present on the polymerized CD unit, wherein the cross-linked polymer is bound to the base biomaterial by at least one of the following mechanisms:

chemical grafting by covalent bonds between the base biomaterial and the cross-linked polymer, physical grafting in the form of a coating resulting from cross-linking of the polymer formed by reaction between the polycarboxylic acid and the cyclodextrin monomer;

wherein the base biomaterial has a porous structure or a non-porous structure, and wherein the device contains said at least one bioactive agent, wherein the bioactive agent forms a complex with the cyclodextrin units, and the bioactive agent is a therapeutic molecule.

2. A device according to claim 1, wherein the base biomaterial is constituted of polymer material, wherein the polymer material is at least one member selected from the group consisting of polyethylene terephthalate glycol (PETG), polylactic acid, polyglycolic acid and copolymers thereof, polyvinylidene fluoride (PVDF), polytetrafluoroethylene (PTFE), polyethylene glycol (PEG), polyamide-6, polyamide-6,6, polypropylene, and polyethylene.

3. A device according to claim 1, wherein the base biomaterial is constituted of a mineral compound, wherein said mineral compound is a bioceramic selected from the group consisting of calcium phosphates, hydroxyapatites, alumina, zirconia, glass, and ionomer glass.

4. A device according to claim 1, wherein the bioactive agent is selected from the group consisting of anticoagulants, antithrombotics, antimitotics, antiproliferation agents, antiadhesion agents, antimigration agents, cell adhesion promoters, growth factors, antiparasitic molecules, antiinflammatories, antifungals, antimicrobial molecules, antiseptics and antibiotics.

5. A device according to claim 1, which is a vascular prosthesis, endoprosthesis or a coated stent; a hernia support; a guided tissue regeneration membrane; a guided bone regeneration membrane; an intrasulcular release device; a dialysis, perfusion, transfusion or artificial nutrition tube or catheter; a transcutaneous implant; a tissue engineering lattice or network; a micro- or macro-porous bone substitute; or suture or bandage wire or thread for medical or veterinary use.

6. A device according to claim 1, wherein the cyclodextrin monomer is at least one member selected from the group consisting of α-cyclodextrin, β-cyclodextrin, γ-cyclodextrin; or the cyclodextrin monomer is at least one member selected from the group consisting of said derivatives of α-cyclodextrin, β-cyclodextrin, γ-cyclodextrin.

7. A device according to claim 1, wherein the poly (carboxylic) acid is selected from the group consisting of acyclic poly (carboxylic) acids, saturated and unsaturated cyclic poly (carboxylic) acids, saturated and unsaturated aromatic poly (carboxylic) acids, hydroxypoly(carboxylic) acids, polyacrylic acid, poly (methacrylic) acid, and anhydride derived from said acids.

8. A device according to claim 1,
wherein the base biomaterial which contains a hydroxyl function and/or an amine function through which the base biomaterial is bound covalently to the cross-linked polymer.

9. A device according to claim 8 wherein the base biomaterial is constituted of polymer material.

10. A device according to claim 9, wherein the polymer material is at least one member selected from the group consisting of cellulose, oxidized cellulose, regenerated cellulose, pectin, carrageenans, alginates and dextrans.

11. A device according to claim 9, wherein the polymer material is at least one member selected from the group consisting of keratin, chitosan, collagen, and gelatin.

12. A method for preparing a device according to claim 1, comprising the steps of:
a) applying to the base material a solid mixture of:
said at least one cyclodextrin monomer,
at least one of said polycarboxylic acid, and
optionally a catalyst;
b) heating the base material provided with the solid mixture at a temperature between 100° C. and 220° C. for a period of 1 to 60 minutes;
c) washing the heated base material provided with the solid mixture with water; and
d) drying the washed base material provided with the solid mixture, wherein at least one bioactive agent is incorporated in the biomaterial by impregnation of the biomaterial after the drying step with a concentrated solution of bioactive agent.

13. A method according to claim 12, wherein the solid mixture is applied by impregnating the base biomaterial with an aqueous solution of:
said at least one cyclodextrin monomer,
at least one of said polycarboxylic acid, and
optionally said catalyst;
and then drying the base biomaterial impregnated with said aqueous solution.

14. A method according to claim 12, further comprising a step of impregnating the biomaterial with a solution of cationic biocidal agent after the drying step.

15. A method according to claim 12, wherein the base biomaterial is constituted of polymer material, wherein the polymer material is at least one member selected from the group consisting of polyethylene terephthalate glycol (PETG), polylactic acid, polyglycolic acid and copolymers thereof, polyvinylidene fluoride (PVDF), polytetrafluoroethylene (PTFE), cellulose, oxidized cellulose, regenerated cellulose, polyethylene glycol (PEG), polyamide-6, polyamide-6,6, polypropylene, polyethylene, keratin, chitosan, collagen, and gelatin.

16. A method according to claim 12, wherein the base biomaterial is comprised of a mineral compound, wherein the mineral compound is at least one member selected from the group consisting of bioceramics and a composite material containing a mineral compound and a polymer material.

17. A method according to claim 16, wherein the bioceramics comprise at least one member selected from the group consisting of calcium phosphates, hydroxyapatites, alumina, zirconia, glass and ionomer glass.

18. A method according to claim 12, wherein the poly(carboxylic) acid is selected from the group consisting of acyclic poly(carboxylic) acids, saturated and unsaturated cyclic poly(carboxylic) acids, saturated and unsaturated aromatic poly(carboxylic) acids, hydroxypoly(carboxylic) acids, polyacrylic acid, poly(methacrylic) acid, and anhydrides derived from said acids.

19. A method according to claim 12, wherein the catalyst is selected from the group consisting of dihydrogen phosphates, hydrogen phosphates, phosphates, hypophosphites, alkaline metal phosphites, polyphosphoric acid alkaline metal salts, carbonates, bicarbonates, acetates, borates, alkaline metal hydroxides, aliphatic and ammonia amines.

20. A method according to claim 12, wherein the cyclodextrin monomer is at least one member selected from the group consisting of α-cyclodextrin, β-cyclodextrin and γ-cyclodextrin; or the cyclodextrin monomer is at least one member selected from the group consisting of said derivatives of α-cyclodextrin, β-cyclodextrin and γ-cyclodextrin.

21. A method according to claim 12, wherein the bioactive agent is at least one member selected from the group consisting of anticoagulants, antithrombotics, antimitotics, antiproliferation agents, antiadhesion agents, antimigration agents, cell adhesion promoters, growth factors, antiparasitic molecules, anti-inflammatories, anti-angiogenics, angiogenesis inhibiters, vitamins, hormones, proteins, antifungals, antimicrobial molecules, antiseptics and antibiotics.

* * * * *